United States Patent [19]  
Fortin et al.

[11] Patent Number: 5,004,754  
[45] Date of Patent: Apr. 2, 1991

[54] BIOFUNGICIDAL COMPOSITION

[75] Inventors: J. André Fortin, Neufchatel; Kelvin K. Ogilvie, Canning; Youla S. Tsantrizos, Ville St-Laurent; Harry H. Kope, Quebec, all of Canada

[73] Assignee: Universite Laval, Cite Universitaire, Canada

[21] Appl. No.: 361,052

[22] Filed: Jun. 5, 1989

[51] Int. Cl.⁵ .................... A01N 37/10; A61K 31/19; C07C 59/84; C07C 59/50
[52] U.S. Cl. .................................. 514/570; 562/459; 562/470
[58] Field of Search ........................................ 514/570

[56] References Cited

U.S. PATENT DOCUMENTS 4,105,783 8/1978 Yu et al. ............................... 514/459
4,246,261 1/1981 Van Scott et al. ................... 514/171
4,363,815 12/1982 Yu et al. ............................... 514/570

FOREIGN PATENT DOCUMENTS 0054174 6/1982 European Pat. Off. ............ 514/570
00273202 7/1988 European Pat. Off. ............ 514/570

Primary Examiner—Lester L. Lee  
Assistant Examiner—Carmen Pili Curtis  
Attorney, Agent, or Firm—Cushman, Darby & Cushman

[57] ABSTRACT

The invention relates to a biofungicidal composition characterized by its capacity to arrest the growth and/or destroy the cell wall of pathogenic fungi, comprises a composition of a compound of the formula I

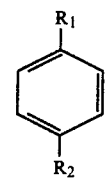

wherein $R_1$ is selected from the group consisting of

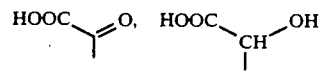

and $R_2$ is —H or —OH and mixtures thereof in association with an inert carrier, and to a method for arresting the growth and/or destroying the cell wall of pathogenic fungi by applying thereto a biofungicidal amount of the composition of a compound of formula I in association with an inert carrier.

9 Claims, No Drawings

BIOFUNGICIDAL COMPOSITION

BACKGROUND OF THE INVENTION

Extracellular antibiotics produced by ectomycorrhizal fungi have been suggested as one form of root protection against infection by phytopathogenic fungi (Zak, Ann. Rev. of Phytopath., 2, pgs. 377-392, 1964).

The production of antibiotic 'in vitro' by mycorrhizal has been reported in over 100 fungi (Marx, Ectomyco., pgs. 351-382, 1973). One such microorganism, *Pisolithus tinctorius*, has been shown to improve the growth of infected plants as described in U.S. Pat. No. 4,550,527.

A number of researchers have tried to isolate an active compound from the liquid culture of the fungus. *Pisolithus tinctorius*. Naphthalenoid pulvinic acid derivatives, a trieterpenoid (pizolactone), humic acid like compounds and others have been isolated from this fungus, but none of them exhibit and suggest an antifungal activity (K. H. Tan et al., Soil Sci. Soc. Am. J., vol. 42, p. 906-908, 1978; M. Gill et al., Phytochemistry, vol. 24, no. 6, pp. 1351-1354, 1985; A. M. Lobo et al., Tetrahedron, vol. 24, no. 21, pp. 2205-2208, 1983). A compound possessing antifungal activity has never been isolated.

Accordingly, since the antifungal activity of *Pisolithus tinctorius* has never been ovserved, there existed no reason for attempting to isolate the biofungicidal factor or factors which are generated in a liquid culture of this fungus.

However, if *Pisolithus tinctorius* produces antibiotic metabolites, it would be highly desirable to find a way of isolating them and using them to destroy undesirable fungi which grow not only on plants but also, for example, on the skin of animals thereby causing dermatomycosis.

SUMMARY OF THE INVENTION

In accordance with the present invention, it has now been discovered that *Pisolithus tinctorius* possesses antifungal activity due to the production of metabolites which have been found to be effective against both phytopathogenic fungi and dermatogenic fungi.

Accordingly the present invention provides a biofungicidal composition characterized by its capacity to arrest the growth and/or destroy the cell wall of pathogenic fungi, which comprises a composition of a compound of the formula I

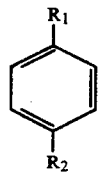

wherein $R_1$ stands for

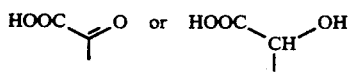

, $R_2$ is —H or —OH and mixtures thereof in association with an inert carrier.

It has been discovered that some of the products falling within the scope of the compounds of formula I, have been isolated from the liquid culture in which *Pisolithus tinctorius* was grown while others are analogues and are obtained through synthesis. Accordingly the liquid culture of *Pisolithus tinctorius* yielded those products of formula I wherein $R_1$ is

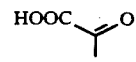

and $R_2$ is —OH, the (R) form of the compound of formula I wherein $R_1$ is

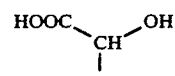

and $R_2$ is OH. On the other hand, the compounds of formula I wherein $R_1$ is

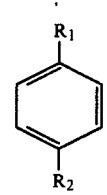

and $R_2$ is —H, the (S) form of the compound of formula I wherein $R_1$ is

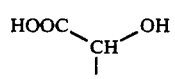

and $R_2$ is —OH, and the (R) and (S) (and (R/S)) forms of the compound of formula I wherein $R_1$ is

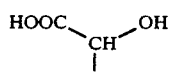

and $R_2$ is —H are analogues of the natural metabolites previously referred to and are obtained by synthetic route.

The isolation and structure determination of the metabolites and the subsequent use of structural analogues thereof make it possible to use of antifungal activity of these compounds for a variety of purposes.

The compositions of the present invention have a long shelf life and do not require maintenance, unlike the extract of *Pisolithus tinctorius*.

The biofungicidal compositions of the present invention are also effective at a low dosage and can be obtained more readily by synthesis than from the extract of the culture of the *P. tinctorius*.

The composition of the present invention causes cell walls deterioration and inhibition of spore germination of pathogenic fungi both of which are important factors in biological control. Unexpectedly, the composition of the present invention causes the bursting of hyphal tips and lateral branch initials on 3 target fungi, two Ascomycetes and one Basidiomycete. Therefore, with the biofungicide compositions of the present invention, the identification of an antagonistic effect can be made more definitive using an obvious phenomena such as the altered hyphal morphology as compared to its usual state.

Since, the beneficial effect of *Pisolithus tinctorius*, as a microorganism, can only be applied to plants via inoculation, there is a great advantage in using the compositions of the present invention. For example, the composition can be used to treat dermatomycosis infection (skin infection).

Other advantages of the present invention will be readily illustrated by referring to the following description.

DETAILED DESCRIPTION OF THE INVENTION

The compounds used in the compositions of the present invention correspond to the general formula I:

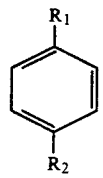   I wherein $R_1$ and $R_2$ are as defined previously.

More specifically, the compounds falling within the scope of formula I are the p-hydroxybenzoylformic acid (IA), the racemic p-hydroxymandelic acid (IB), the indivual S-, R-isomer (IC,ID respectively), the indivual S-, R-isomer of mandelic acid (IE,IF respectively) and benzoylformic acid (IG) thereof, and also mixtures thereof.

The p-hydroxybenzoylformic acid (IA) may be obtained by the method described by Shouteeten Alain et al. (Chemical Abstract, 96 (25): 2174812). The biologically inactive sodium salt of this product is commercially available from Aldrich Chemical Co. It can also be extracted from the growth liquid of *Pisolithus tinctorius*.

The synthesis of the optically enhanced p-hydroxymandelic acid (IC,ID) can be made in accordance with the procedure described in example III. The racemic mixture is commercially available from Aldrich Chemical Co., or it can be obtained by the synthetic method described in the French Patent application No. 2,495,137, which was published on June 4, 1982. Unfortunately, a simple method of separating the (R)-isomer from the (S)-isomer is not available, therefore, if one isomer is desired specifically, it must be synthesized.

The (S) p-hydroxymandelic acid (IC) can be obtained by the synthetic method fully described in example III, and using p-hydroxybenzylformic acid as the starting material.

The natural metabolites (IA,ID) may be extracted by the method outline in example II. The end products were found to be, substantially pure, as relatively stable white solids.

Since nature only produces the (R) isomer in the liquid culture of *Pisolithus tinctorius*, the (S) p-hydroxymandelic acid (ID) can be successfully synthetized using the method described in example II.

As a carrier, the active ingredient may be formulated as a cream, a lotion, an ointment, as well as a dusting powder or a spray. As a cream or ointment, soft parrafin and lanolin or derivative or synthetic equivalent thereof may be used. The term 'soft parrafin' as used herein includes the cream or ointment bases white soft parrafin and yellow soft paraffin. The term 'lanolin' as used herein includes native wool fat and purified wool fat. Derivatives of lanolin include, in particular, lanolins which have been chemically modified in order to alter their physical or chemical properties. Synthetic equivalents of lanolin include, in particular, synthetic or semi-synthetic compounds and mixtures which are known and used in the pharmaceutical and cosmetic arts as alternatives to lanolin and may, for example, be referred to as 'lanolin substitutes'.

A suitable composition comprises from 25 to 99% of the soft paraffin, preferably from 50 to 98%, more preferably from 75 to 95%. Suitably the composition comprises the lanolin or derivative or synthetic equivalent thereof in an amount of from 1 to 25%, preferably from 1 to 15%, more perferably from 3 to 7%. In addition, such a composition may contain liquid paraffin in an amount of from 0 to 20%. The term 'liquid paraffin' as used herein includes any form of liquid paraffin suitable for pharmaceutical or veterinary topical use.

Suitable compositions of the present invention comprise one of the following compound or mixture thereof in association with an inert carrier:

1—(IA) at a concentration of 60–120 µg/ml or more
2—(IB) at a concentration of 60 µg/ml or more
3—(IC) at a concentration of 30 µg/ml or more
4—(ID) at a concentration of 60–120 µg/ml or more
5—(IE) at a concentration of 30 µg/ml or more
6—(IF) at a concentration of 120 µg/ml or more.

The inert carrier is any carrier used for applying fungicides to plants or any topical carrier used for application to the skin.

EVIDENCE OF UTILITY

The biofungicidal activity of Product IA, IB, IC, ID, IE and IF was compared with an extract of the liquid culture of *P. tinctorius*, and found to be the same.

The spectrum of activity of *P. tinctorius* was examined first, using a test comprising a variation of the agar method of Dennis & Webster (Transactions of the British Mycological Society, 57, pgs. 25–39, 1971) in screening for fungal antagonism. A plug was cut from under a two week old colony of a *P. tinctorius* culture grown on a nucleopore filter. This cell free extract plug was placed on a fresh agar plate and the test fungi were placed at a distance from the plug. The method gave a cell free exudate of released compounds from the ectomycorrhizal fungus. The zone of inhibition was determined by measuring, in a straight line from the edge of the confronted colony to the edge of the confronted plug. Growth of the test fungi on control plates was used to determine the number of days the plates had to be incubated in measuring a zone of inhibition effectively. Three replicates were made for each confrontation tested. All colonies of the test fungi were examined in situ for microscopical changes to their hyphal morphology.

*P. tinctorius* had a large spectrum of activity, inhibiting the growth of many phytopathogenic and dermatogenic fungi that were tested.

The potency of the natural compound and their analogues were investigated next. The exact concentrations for activity were determined using the phytopathogenic fungus: *Truncatella hartigii*. The 50% inhibition concentrations for spore germination were determined using multiple tests (10 samples of 10 conidia each). The effective concentrations were set at the value where less than 50% of spore germination was observed as compared to the control.

Although nature makes the (R)-enantiomer the synthetic analogue (S) was found to be more active. These results are in agreement with those obtained with mandelic acid. All results are reported in Table 1 and 2 below.

TABLE 1

Hyphal Lysis & 50% Germination Inhibiton: Natural Compounds Minimum concentration required for activity

|    | hyphal lysis | <50% spore germination |
|----|--------------|------------------------|
| IA | 60–120 µg/ml | 30–60 µg/ml            |
| ID | 60–120 µg/ml | 30–60 µg/ml            |

TABLE 2

50% Germination Inhibiton: Analogues Minimum concentration required for activity

|                                                  | <50% spore germination |
|--------------------------------------------------|------------------------|
| p-hydroxymandelic acid (R/S)                     | 60 µg/ml               |
| p-hydroxymandelic acid (R) 33% enantiomeric excess | 70 µg/ml             |
| p-hydroxymandelic acid (S) 60% enantiomeric excess | 30 µg/ml             |
| 100% pure mandelic acid (R)                      | 120 µg/ml              |
| 100% pure mandelic acid (S)                      | 30 µg/ml               |

REAGENTS AND CHEMICALS:

The sodium p-hydroxybenzoylformate salt, (S) and (R) mandelic acid, benzoylformic acid and the racemic p-hydroxymandelic acid are sold by Aldrich Chemical Co. Doubly distilled water and HPLC grade methanol are filtered through a 0.45 u filter membrane (Millipore Corp. Bedford, Mass.) before they are used for HPLC. Chromatographic solvents are fractionally distilled prior to use with the exception of acetic acid.

CHROMATOGRAPHY:

Silica gel chromatography is performed on Merck Kieselgel 60 (230–400 mesh, no. 9385) using flash chromatography. Cellulose thin-layer chromatography (TLC) is performed on Eastman cellulose (Eastman Kodak Co., no. 13254) plates (0.16 mm thickness), where for column chromatography CF 11 Whatman powder (American Chemicals LTD. Montreal, QUE.) is used. Paper chromatography is performed on Whatman paper sheets 3 mm Chr.

HPLC analysis and purifications are carried out on a Waters instrument (pump model 501, variable wavelength detector model 450, U6K injector). Two reverse phase $C_{18}$ columns are used; Whatman Partisil 5 ODS 3 (10 cm×9.4 mm ID, 5 um particles, Chromatographic Specialties Inc.) and CSC-S ODS2 (25 cm×9.4 mm ID, 5 um particles, Chromatographic Specialties Inc.) and CSC-S ODS2 (25 cm×9.4 mm ID, 5 um particles, Chromatography Science Company Inc., Montreal, QUE.)

SPECTRA:

Ultraviolet spectra are recorded on a Hewlett Packard 8451A DIODE ARRAY Spectophometer. Nuclear Magnetic Resonance are obtained at 20°–2° C. using Varian XL-200, XL-300 and Bruker 500 MHz instruments. $^1H$ and $^{13}C$-NMR chemical shifts are quoted in ppm and are referenced to the internal deuterated solvent downfield from tetramethylsilane (TMS). The samples used for $D_2O$—NMRs are first dissolved in ~1 mL of 99.8% $D_2O$ and lyophilized two times before their data is recorded in 99.96% $D_2O$.

EXAMPLE I

Preparation of the liquid culture and the filtered culture liquid of *Pisolithus tinctorius*

Four, 6 mm disks from the edge of a *Pisolithus tinctorius* (C.R.B.F. #0039) colony growing on MNM agar were inoculated into 250 mL Erlenmeyer flasks containing 100 mL of liquid MNM (Marx, 1969). The solution was buffered with 0.1M sodium citrate/citric acid buffer, pH 5.5, and grown at 25° C. on a rotary shaker at 100 rpm. After incubation for 45–50 days the culture liquid was passed through a 0.2 µm filter and used in the tests described below. The filtered culture liquid of *P. tinctorius* had a measured pH of 3.8 after 45–50 days growth.

EXAMPLE II

General extraction and isolation of active crude

The filtered culture liquid of Example I is filtered through several layers of cheese-cloth to remove the myclium. The dark brown liquid culture is reduced in volume (~1/5) under high vacuum at 40° C. The remaining water is removed by freeze-drying to give a solid, the yields of which vary from 2.5 to 4.3 grams per liter of original culture.

Soxhlet extraction of the above solid with USP diethyl ether (500 mL/day, 15 g) over a period of 2–3 days gives a light orange oil upon evaporation of the solvent. A small amount of glucose often crystallizes out of the ether solution which is filtered off. The yields of biologically active material range from 7 to 60 mg per gram of solid (average=33 mg/g) but can be increased if the extraction is allowed to continue for up to 7 days. A longer period of extraction, however, leads to the isolation of a much darker crude whose subsequent purification is much more difficult.

Further purification is carried out on a tightly packed column (using air pressure) of Whatman Cf11 cellulose powder, applied as a slurry in ethanol. Once the crude toxin is applied to the top of the column, a solvent mixture of 95% n-butanol saturated with water-5% glacial acetic acid is allowed to filter through by gravity. Cellulose TLC is used to follow the elution of active metabolites (compound I Rf~0.28, compound II Rf~0.33 in isopropanol/0.5M $NH_4HCO_3$).

The majority of middle fractions are combined and rechromatographed on paper (Whatman 0.33 mm). Elution of the paper with isopropanol/0.5M $NH_4HCO_3$ (4/1) for a total length of ~40 cm (12–15 h) separates the mixture into five bands: at 0.05–0.1 (yellow), 0.22–0.32 (active mixture), 0.32–0.4, 0.4–0.56 (fluorescent) and at 0.55–0.65. All bands are cut, dried, eluted with doubly distilled water and freeze-dried. The active material is obtained as a light brown solid, average yield 30–35 um/mg of crude. The final purification through descending paper chromatography is eluted with 95% n-butanol saturated with paper-5% acetic acid. After 15 h the two active compounds have separated at Rf values of 0.2–0.6 (comp.I) and Rf 0.6–0.7 (comp.II). The visualization of these bands is difficult and it could only be done in a completely dark room under uv light. The strip of paper impregnated with the antifungal compounds are cut and dried in a desicater, under high vacuum. Elution of the papers with doubly distilled water followed by freeze-drying leads to the isolation of p-hydroxybenzoylformic acid (IA) and p-hydroxymandelic acid (IC).

Final purification is carried out on a reverse phase ($C_{18}$) HPLC column (CSC-S ODS2, 25 cm×9.4 mm ID, 5 um particles) using a solvent mixture of 91.74% $H_2O$/7.34% $CH_3OH$/0.92% $CH_3COOH$ at a flow rate of 2.0 mL/min. P-hydroxybenzoylformic acid and p-hydroxymandelic acid have retention times 5–6 min and 8–9 min respectively.

P-hydroxybenzoylformic acid:

Since the sodium salt of this compound turns out to be commercially available, the $^1H$ and $^{13}C$-NMR spectras, of both the actual compounds (Table 3) and their methyl esters (Table 4), are compared. All spectral data, including uv in acid and base, are found to be identical. It should be noted that the carbon chemical shifts vary with the pH of the solution most notably so for the two carbonyl carbons (Table 3).

TABLE 3

NMR data of compound IA vs commercial p-hydroxybenzoylformic acid $^1H$ NMR: (DMSO, 200 MHz, S-values, solvent as internal standard)

|  | Compound IA | p-Hydroxybenzoylformic acid |
|---|---|---|
| ($2H_4$,d, J = 8.0 Hz) | 6.9 | 6.8 |
| ($2H_4$,d, J = 8.0 Hz) | 7.7 | 7.7 |
| [—OH,s(br.)] | 10.7 | 10.7 |

$^{13}H$ NMR: (DMSO, 300 MHz, S-values, solvent as internal standard)

|  | Compound IA | | p-Hydroxybenzoylformic acid | |
|---|---|---|---|---|
|  | salt | acid | salt | acid |
| $C_1$ | 170.2 | 166.8 | 170.2 | 166.8 |
| $C_2$ | 194.3 | 187.0 | 194.5 | 187.0 |
| $C_3$ | 125.7 | 123.3 | 125.6 | 123.3 |
| $C_4$ | 131.5 | 132.2 | 131.5 | 132.3 |
| $C_5$ | 115.1 | 116.0 | 115.2 | 116.0 |
| $C_6$ | 162.1 | 163.8 | 162.2 | 163.9 |

TABLE 4

NMR data of compound IA vs commercial p-hydroxybenzoylformic acid and methyl esters.

$^1H$ NMR: (CDCl$_3$, 200 MHz, S-values, solvent as internal standard)

Methyl ester derivatives

|  | Compound IA | p-Hydroxybenzoylformic acid |
|---|---|---|
| ($2H_4$,d, J = 8.9 Hz) | 6.9 | 6.8 |
| ($2H_5$,d, J = 8.9 Hz) | 7.9 | 7.9 |
| [—OH,s(br.)] | ~6.7 | ~6.6 |
| ($CH_3$,s) | 3.9 | 3.9 |

$^{13}H$ NMR: (CDCl$_3$, 300 MHz, S-values, solvent as internal standard)

Methyl ester derivatives

|  | Compound IA | p-Hydroxybenzoylformic acid |
|---|---|---|
| $CH_3$ | 52.8 | 52.9 |
| $C_1$ | 164.4 | 164.6 |
| $C_2$ | 184.8 | 185.0 |
| $C_3$ | 125.4 | 124.9 |
| $C_4$ | 133.0 | 133.2 |
| $C_5$ | 115.9 | 116.1 |
| $C_6$ | 162.0 | 162.7 | p-Hydroxymandelic acid Compound ID:

The $^1H$ NMR of compound (ID) in $D_2O$ shows three types of non-exchangeable protons; two doublets at 7.13 ppm and 6.72 ppm (J=8.2 Hz), characteristic of a para-substituted aromatic ring, and a broad singlet at ~5.0 ppm (integration of 2:2:1 respectively). Since it is nearly impossible to free the sample of water, the $^1H$ NMR in DMSO fails to reveal the presence of any exchangeable protons.

$^{13}H$ NMR (FIG. 9) in $D_2O$+DMSO reveals the presence of six types of carbons; at 74.4 ppm (probably a C—OH), two very intense signals at 117.3, 130.4 ppm, weak signals at 132.3 ppm, 157.5 ppm (phenolic carbon) and 177.5 ppm (most likely carboxylic acid). Distortionless Enhancement by Polarization Transfer (DEPT) NMR indicate that the carbon at 74.4 ppm has one proton attached to it.

No satisfactory mass spectra can be obtained either with CI($NH_3$) or FAB. $^{252}Cf$-plasma desorption mass spectometry[21a-c], however, suggested a mass of 168.1. An electrosprayed sample gives a positive ion at 323.2 ($M^{2-}+H+2Na^+)^+$ and a negative ions at 167.1 ($M^{2-}+H^+)^-$. These results are further supported by the ions obtained from the $^{252}cf$-plasma desorption spectra of a sample adsorbed onto a tridodecylmethylammonium chloride (TDMAC) cationic surfactant; 167.1 ($M^{2-}+H^+)^-$, 869.9 [(TDMA$^+$)($M^{2-}+H^+)_2^-]^-$, 1776.6 [(TDMA$^+)_3M^{2-}$] and 121.1 ($M^{2-}$—H-$CO^{2-}H)^-$.

Given the close similarities of spectral data between compounds IA and ID and the difference of only two mass units between their respective molecular ions, the structure of p-hydroxymandelic acid (ID) is proposed. A commercial sample of S/R p-hydroxymandelic acid is used to compare spectral data. As expected, all sets of data are identical and only the chirality of the natural product remains to be determined.

The metabolite (ID) was shown to be the R-enantiomer of p-hydroxymandelic acid, by synthesizing both enantiomers using the method outlined in example III and comparing their optical rotation properties.

EXAMPLE III

Method of synthesizing optically active p-hydroxymandelic acid (S) and (R) (IC, ID)

Synthesis of optically active p-hydroxymandelate ester (R)-(+)-BINAL-H and (S)-(−)-BINAL-H reagent are prepared following the procedure developed by Noyori et al. (J. Am. Chem. Soc., 106, 6709–6716 (1984)). These reagents are used to synthesize the (S) and (R) isobutyl-p-hydroxymandelate esters respectively.

Isobutyl-p-hydroxybenzoylformate 18 (603 mg. 2.72 mmoles) dissolved in dry THF (15 mL) is added dropwise into a (R)-(+)-BINAL-H reagent solution (4 eq) at −78° C. over a period of 10–15 min. The reaction is stirred at −78° C. for 3.5 h and quenched with 3 eq of glacial acetic acid (~0.5 mL, the excess hydride is estimated to be ~3 eq). EtOAc (100 mL) and $H_2O$ (50 mL) are added, the mixture is filtered through celite and allowed to separate at room temperature. The EtOAc layer is removed, the aqueous layer is further adjusted to pH 6–7 and reextracted with EtOAc (3×, 50 mL).

Flash column chromatography of the organic layer with Pet. Ether/EtOAc (3:1) afforded the (S) enantiomer of compound 15 (15 b, 90 mg, 15% yield after chromatography) in ~60% enantiomeric purity (as determined by NMR), a major side product (40 mg, 10% yield), binapthol and unreacted starting material.

p-hydroxymandelate ester:

TLC: Pet. Ether/EtOAc (3:1), Rf=0.18.
[α]D= +28.7

$^1$H NMR and $^{13}$C NMR are identical to the racemic 16, however in the presence of (S)-(+)-2,2,2-trifluoro-1-(9-anthryl)ethanol (1.5-2 eq) the proton spectra (300 MHz) clearly shows two sets of peaks for the C-2 proton; the (S) enantiomer upfield from the (R) with integration of S/R= ~4/1, hence enantiomeric purity of 60% was established.

A major side product of the reaction:

TLC: Pet. Ether/EtOAc (3:1), Rf-0.08.
$^1$H NMR (acetone-d$_6$, 200 MHz): 4.79 (s, 2H, CH$_2$), 6.95 and 7.87 (dd, 4H, Ar), exchangeable protons are not seen.
$^{13}$C NMR (acetone-d$_6$, 300 MHz): 65.6 (C-1), 116.3 (2C-4), 127.1 (C-3), 131.1 (2C-5), 163.9 (C-6) and 198.6 (C-2).
APT $^{13}$C NMR for quaternary carbons: 127.1, 163.9 and 198.6 DEPT NMR; 0 CH$_3$, 1 CH$_2$ at 65.6 and 2 CHS at 116.3 and 131.1.

Hydrolysis of p-hydroxymandelate ester to the p-hydroxymandelic acid:

To a solution of p-hydroxymandelate ester (60 mg, 0.27 mmoles) in dioxane (3 mL) 2 eq of NaOH are added (1M solution, 535 uL). The reaction is stirred at room temperature for 15 h, at which point 10 mL of H$_2$O are added and the pH is adjusted to ~6.5 with 0.1N HCl. The aqueous layer is extracted with EtOAc (3×15 mL) in order to remove unreacted starting material. The aqueous layer is evaporated to dryness under high vacuum at 40° C., re-dissolved in H$_2$O (~15 mL) and passed through an ion exchange resin (Dowex 50W—X8, H$^+$, 20-50 Mesh) in order to remove Na$^+$. The free p-hydroxymandelic acid is isolated in 90% yield (41 mg).

Its optical rotation, [α]D= −10.2°, is compared to that of natural product 2, [α]D= −2.7°.

Although it is concluded that the p-hydroxymandelic acid metabolite (ID) must have the (R) absolute configuration, the values for the optical activity obtained are not accurate; compound (ID) is acidic enough to catalyze, in solution, its own racemization.

We claim:
1. A method of destroying phytopathogenic fungi which comprises administering to a plant infected with said fungi at a concentration of at least 30 μg/ml a compound of formula I:

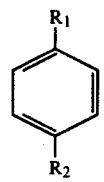

wherein R$_1$ is selected from the group consisting of

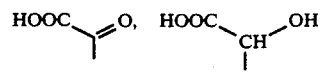

R$_2$ is —H or —OH and mixtures thereof.

2. A method of destroying phytopathogenic fungi according to claim 1 wherein the compound of formula I is the racemic mixture of p-hydroxymandelic acid.

3. A method of destroying phytopathogenic fungi according to claim 1 wherein the compound of formula I is the racemic mixture of mandelic acid.

4. A method of destroying phytopathogenic fungi according to claim 1 wherein the compound of formula I is the (R)-isomer of p-hydroxymandelic acid.

5. A method of destroying phytopathogenic fungi according to claim 1 wherein the compound of formula I is the (R)-isomer of mandelic acid.

6. A method of destroying phytopathogenic fungi according to claim 1 wherein the compound of formula I is the (S)-isomer of p-hydroxymandelic acid.

7. A method of destroying phytopathogenic fungi according to claim 1 wherein the compound of formula I is the (S)-isomer of mandelic acid.

8. A method of destroying phytopathogenic fungi according to claim 1 wherein the compound of formula I is p-hydroxybenzoylformic acid.

9. A method of destroying phytopathogenic fungi according to claim 1 wherein the compound of formula I is benzoylformic acid.

* * * * *